United States Patent [19]

Sciavolino

[11] 4,069,379
[45] Jan. 17, 1978

[54] SEMI-SYNTHETIC OLEANDOMYCINS

[75] Inventor: Frank C. Sciavolino, East Lyme, Conn.

[73] Assignee: Pfizer Inc., New York, N.Y.

[21] Appl. No.: 709,703

[22] Filed: July 29, 1976

Related U.S. Application Data

[63] Continuation-in-part of Ser. No. 703,464, July 8, 1976, abandoned, which is a continuation-in-part of Ser. No. 663,467, March 3, 1976, abandoned.

[51] Int. Cl.$^2$ ............................................. C07H 17/08
[52] U.S. Cl. .......................................... 536/9; 424/180
[58] Field of Search ....................................... 536/9, 17

[56] References Cited

U.S. PATENT DOCUMENTS 3,853,842  12/1974  Kishi et al. ............................. 536/17
3,975,372  8/1976  Ganguly et al. ........................ 536/17

OTHER PUBLICATIONS

LeMahieu et al., "The Jour. of Antibiotics", vol. XXIX, No. 7, July 1976.

*Primary Examiner*—Johnnie R. Brown
*Attorney, Agent, or Firm*—Connolly and Hutz

[57] ABSTRACT

Disclosed herein is a novel series of semi-synthetic oleandomycins having an exocyclic methylene or a cyclopropyl group at the $C_8$ position. Processes for preparing the methylene compounds from the natural oleandomycins and the cyclopropyl compounds from the methylene compounds are also disclosed.

The oleandomycin compounds of the present invention are effective in inhibiting the growth of microorganisms, especially Gram-positive microorganisms.

8 Claims, No Drawings

SEMI-SYNTHETIC OLEANDOMYCINS

CROSS-REFERENCE TO RELATED APPLICATIONS

This application is a continuation-in-part of copending application Ser. No. 703,464, filed July 8, 1976, which in turn is a continuation-in-part of copending application Ser. No. 663,467 filed Mar. 3, 1976, both now abandoned.

BACKGROUND OF THE INVENTION

Oleandomycin, its production in fermentation broths and its use as an antibacterial agent were first described in U.S. Pat. No. 2,757,123, the disclosure of which is incorporated herein by reference. The naturally occurring compound is known to have the structure:

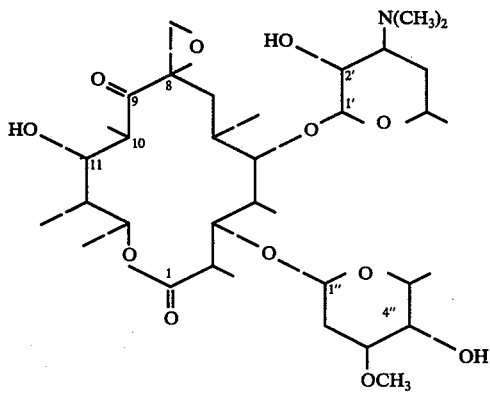

The conventionally accepted number scheme is shown at a variety of positions. Several synthetic modifications of this compound are known, particularly those in which from one to three of the free hydroxyl groups found at the 2', 4" and 11-positions are esterified as acetyl esters. There are described in U.S. Pat. No. 3,022,219 other modifications in which the acetyl in the above-mentioned esters is replaced with another, preferably unbranched alkanoyl having from two to six carbon atoms or trifluoroacetyl moiety.

Also known are semi-synthetic oleandomycins in which one or several of the hydrogens of the hydroxyl groups mentioned above are replaced with a tri(lower alkyl)silyl and preferably a trimethyl silyl group.

SUMMARY OF THE INVENTION

This invention is concerned with a semi-synthetic oleandomycin of the formula:

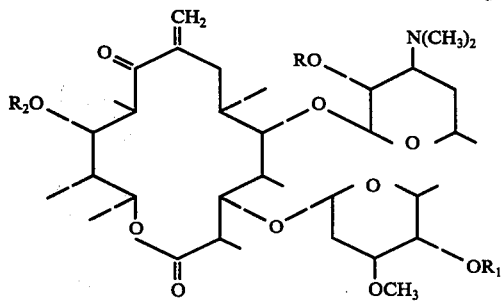

and the non-toxic acid addition salts thereof wherein R is selected from the group consisting of hydrogen and alkanoyl having from two to three carbon atoms; $R_1$ is selected from the group consisting of hydrogen, alkanoyl having from two to three carbon atoms and tri (lower alkyl) silyl; and $R_2$ is selected from the group consisting of hydrogen, alkanoyl having from two to three carbon atoms, trifluoroacetyl and tri (lower alkyl) silyl.

This invention is also concerned with a $C_8$-cyclopropyl compound of the formula:

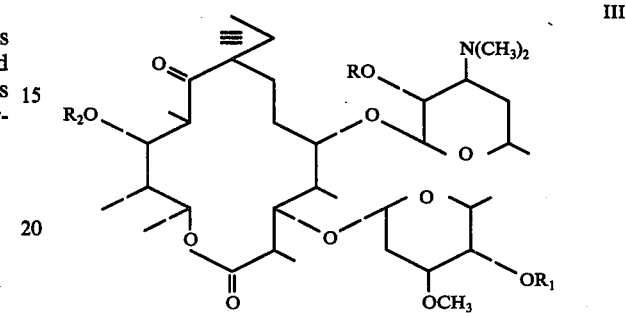

and the non-toxic acid addition salts thereof wherein R is selected from the group consisting of hydrogen and alkanoyl having from two to three carbon atoms; and $R_1$ and $R_2$ are selected from the group consisting of hydrogen, alkanoyl having from two to three carbon atoms and tri (lower alkyl) silyl.

DETAILED DESCRIPTION OF THE INVENTION

Oleandomycin and triacetyl oleandomycin are presently useful members of the armamentarium of antibiotics for the treatment of bacterial infections. It has now been found that synthetic derivatives of oleandomycin of Formula II where R is selected from the group consisting of hydrogen and alkanoyl having from two to three carbon atoms; $R_1$ is selected from the group consisting of hydrogen, alkanoyl having from two to three carbon atoms, and tri(lower alkyl)silyl; and $R_2$ is selected from the group consisting of hydrogen, alkanoyl having from two to three carbon atoms, trifluoroacetyl and tri(lower alkyl)silyl; and synthetic derivatives of oleandomycin of Formula III wherein R is selected from the group consisting of hydrogen and alkanoyl having from two to three carbon atoms; $R_1$ is selected from the group consisting of hydrogen, alkanoyl having from two to three carbon atoms and tri(lower alkyl)silyl; and $R_2$ is selected from the group consisting of hydrogen, alkanoyl having from two to three carbon atoms and tri(lower alkyl)silyl are useful as antibiotics for the treatment of bacterial infections.

The term lower alkyl as used herein in reference to compounds of this invention refers to those branched and unbranched alkyl radicals of from one to six carbon atoms.

A compound of Formula II is prepared from a compound of the formula:

IV

-continued

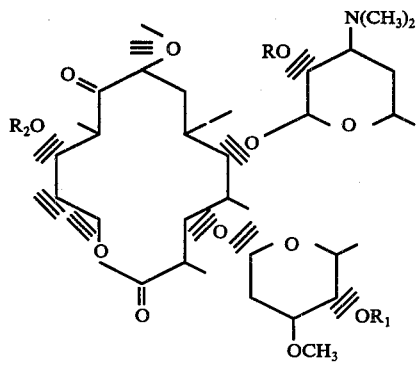

wherein R, R₁ and R₂ are selected from the group consisting of hydrogen and alkanoyl having from two to three carbon atoms. The reduction of the epoxide group to an exocyclic methylene is accomplished by contacting a compound of Formula IV dissolved in a reaction-inert and preferably water miscible solvent with lower valence state transition metal ions such as $Cr^{+2}$, $Ti^{+3}$ or $V^{+2}$ dissolved in water. Acetone, a lower alkanol or tetrahydrofuran are preferred as the reaction-inert solvents and $CrCl_2$ is the preferred source of lower valence state transition metal ions.

A solution of chromous chloride, prepared by treating a hydrochloric acid solution of chromium trichloride with zinc dust and mercuric chloride, is added to a flask under a carbon dioxide atmosphere along with simultaneous addition of an acetone solution of a compound of Formula IV wherein R, R₁ and R₂ are preferably hydrogen and/or acetyl. The additions are made over a period of 10 to 20 min. After stirring at room temperature for 20 to 40 minutes, water and ethyl acetate are added and the stirring continued for an additional 10 to 20 minutes. The ethyl acetate phase is separated, washed with water and sodium bicarbonate at pH 8.5, dried and concentrated under vacuum to yield a compound of Formula II.

A compound of Formula II with a trifluoroacetoxy group at the 11-position may be prepared by contacting a compound of Formula II where R₂ is hydrogen and R and R₁ are alkanoyl having from two to three carbon atoms with trifluoroacetic anhydride at 5°–10° C. in the presence of pyridine and the reaction allowed to proceed overnight at room temperature. The reaction mixture is concentrated to an oil and poured onto a mixture of ice and ethyl acetate. The aqueous phase is adjusted to pH 8.5 with aqueous sodium bicarbonate and the ethyl acetate phase separated, washed with water, dried and the solvent evaporated under reduced pressure.

A compound of Formula II with a tri(lower alkyl)-silyloxy group at the 11-position may be prepared by contacting a compound of Formula II where R₂ is hydrogen and R and R₁ are alkanoyl having from two to three carbon atoms with a tri(lower alkyl)silyl chloride in the presence of imidazole and dimethylformamide at room temperature. After the addition of water and ethyl acetate and adjustment to pH 10.5, the organic phase is separated, washed, dried and evaporated under reduced pressure.

A cyclopropyl moiety is introduced by contacting a compound of Formula II wherein R and R₁ are acetyl and R₂ is selected from the group consisting of alkanoyl having from two to three carbon atoms and tri(lower alkyl)silyl with at least a substantial equivalent of dimethylsulfoxonium methylide in a reaction-inert solvent under an inert atmosphere such as nitrogen. A preferred reaction-inert solvent is a substantially anhydrous mixture of tetrahydrofuran and dimethylsulfoxide. Molar amounts of trimethylsulfoxonium iodide and 50% oil dispersion of sodium hydride are placed in a flask to which is added dimethylsulfoxide over a 5 to 10 minute period with cooling in an ice/water bath. The reaction mixture is allowed to come to room temperature until the evolution of hydrogen ceases. A solution of a compound of Formula II and dimethylsulfoxide is added dropwise and the reaction allowed to proceed at room temperature for about an hour. The solution is poured into water/ethyl acetate and the aqueous phase adjusted to pH 9.0. The organic phase is separated, washed with water, dried and evaporated to dryness under reduced pressure.

The pharmaceutically acceptable acid addition salts of the semi-synthetic oleandomycins of the present invention may be prepared by contacting a solution of a compound of Formula II or Formula III in a suitable solvent such as acetone with a stoichiometric equivalent of a mineral acid such as hydrochloric, hydrobromic, phosphoric or sulfuric acid; an organic acid selected from the group consisting of aspartic, citric, tartaric, gluconic, succinic and stearic acid; or an alkyl sulfuric acid such as lauryl sulfuric acid. The salt precipitates afte the neutralization reaction or, if necessary, after partial evaporation of the reaction solution. The product may be recovered by filtration, centrifugation or lyophilization.

The oleandomycin compounds of the present invention are effective in inhibiting the growth of microorganisms, especially Gram-positive microorganisms. The high activity against Gram-positive organisms shown by these compounds is contrasted in some respects with the lower activity against Gram-negative organisms. The following table illustrates the in vitro antibiotic spectrum of the compounds of the instant invention. The tests were run according to the "minimum inhibitory concentration"(MIC) procedure of Ericsson and Sherris [H. M. Ericsson and J. C. Sherris, *Acta. Pathol. Microbiol. Scand. Suppl.*, 217B 64 (1971)].

TABLE I.

MIC Values (mcg./ml.) of some Semi-Synthetic Oleandomycins

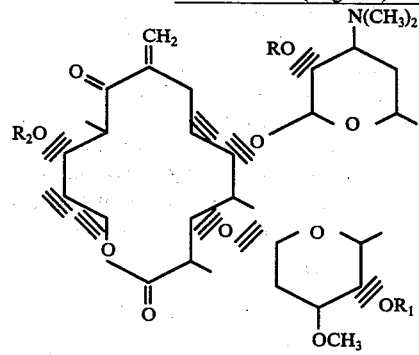

II

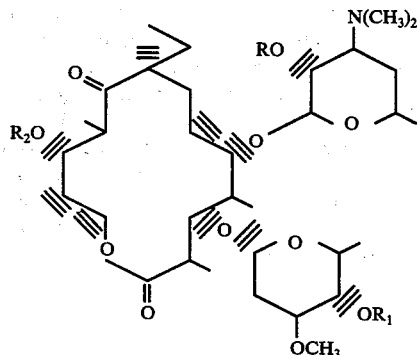

III

| Compound | R | $R_1$ | $R_2$ | Staph. aureus 01A005* | Staph. aureus 01A400R* | B. subtilis* | E. coli 51A266+ | Klebsiella pn. 53A009+ | Salm. typhm. 58D009+ |
|---|---|---|---|---|---|---|---|---|---|
| II | Ac | H | Ac | 3.12 | >200 | 3.12 | >200 | >200 | >200 |
| II | H | H | H | 6.25 | 25 | — | >200 | >200 | — |
| II | Ac | Ac | Ac | 25 | 200 | — | >200 | >200 | >200 |
| II | Ac | Ac | $CF_3C(O)$ | 25 | 200 | 25 | >200 | >200 | >200 |
| III | Ac | H | Ac | 0.20 | 3.12 | 0.78 | >200 | >200 | >200 |
| III | H | H | H | 0.20 | 1.56 | 0.39 | >200 | >200 | >200 |
| III | Ac | Ac | Ac | 1.56 | 12.5 | 3.12 | >200 | >200 | >200 |
| III | Ac | Ac | $Me_3Si$ | 3.12 | >200 | 12.5 | >200 | >200 | >200 |

*= Gram-positive
+ = Gram-negative

The ability of the compounds of the present invention to protect against in vivo infections was determined by subcutaneous or oral administration to mice infected with Staph. aureus 01A005. Using the test method described by Retsema [J. A. Retsema et al., *Antimicr. Agents and Chemother.*, 9, 975 (1976)], it was determined that, in particular, compounds II and III wherein R, $R_1$ and $R_2$ are each hydrogen both gave protection against infection which was comparable to natural oleandomycin.

For effective prophylactic and anti-infectious in vivo use, the semi-synthetic oleandomycin compounds of the present invention may be administered either alone or in combination with a pharmaceutically-acceptable carrier and by both the oral and parenteral routes. The ultimate choice of route and dose is made by the attending physician and is based upon the patient's unique condition. However, the usual dosage for administration to humans may be in the range of approximately 500–2000 mg. per day, and preferably in about one to four doses. However, this dosage may vary somewhat with the weight of the subject being treated; in general, about 10–40 mg./kg. of body weight per day may be employed.

In order to use the compounds of this invention, they may be combined with inert pharmaceutical excipients such as lactose, mannitol and starch, and formulated into dosage forms such as tablets, capsules and the like. For parenteral administration, these compounds may be formulated with an inert, parenterally acceptable vehicle such as water, saline, sesame oil, propylene glycol and the like. These various pharmaceutical dosage forms are compounded by methods well known to the pharmacist's art.

EXAMPLE I 8,8a-Deoxy-8,8a-Methylene-2',4"-Diacetyloleandomycin

A 5 liter, three-necked round bottom flask was charged with zinc dust (200 g) and mercuric chloride (20 g). After the solids were mixed well, 1N HCl (500 ml) was added and the mixture was stirred vigorously for 15 min. The aqueous supernate was removed and fresh 1N HCl (500 ml) added and the flask placed under a carbon dioxide atmosphere. A filtered solution of chromium trichloride (1 kg in 1300 ml of 1N HCl) was added rapidly to the zinc amalgam. The mixture was stirred under a carbon dioxide atmosphere for 1 hr during which time a light blue color developed indicating the presence of chromous chloride ($CrCl_2$). Stirring was discontinued after 1 hr and the zinc amalgam allowed to settle to the bottom of the flask.

A solution of 2',4"-diacetyloleandomycin hydrochloride (500 g) in acetone (3.5 l) and water (1.75 l) was placed in a dropping funnel attached to a 12 liter, three-necked round bottom flask equipped with an overhead mechanical stirrer. To this flask was added, under a carbon dioxide atmosphere and with stirring, the solution of 2',4"-diacetyloleandomycin hydrochloride and the previously prepared solution of chromous chloride. The solutions were added simultaneously at such a rate that both finished at the same time. The addition took about 12 minutes. After 35 min. of stirring at room temperature, water (2 l) and ethyl acetate (2 l) were added to the reaction and stirring continued for 15 min. The ethyl acetate layer was separated and washed with water (1600 ml). The ethyl acetate was separated and the aqueous extracts combined and washed with fresh ethyl acetate (2 l). The ethyl acetate layer was separated and washed with water (1.7 l). The organic phase was separated and the aqueous washes combined and treated with sodium chloride (1500 g). The additional ethyl acetate which separated was syphoned off and combined with the other ethyl acetate extracts. Water was added to the combined ethyl acetate extracts and adjusted to pH 8.5 with sodium bicarbonate. The organic layer was separated washed with water, saturated sodium chloride and dried over anhydrous sodium sulfate. Filtration and evaporation of the solvents under reduced pressure afforded a white solid which was crystallized from ethyl acetate/heptane to give the title compound (237 g, mp 184°–186° C.)

Elemental Analysis

|  | C | H | N |
|---|---|---|---|
| Calculated | 61.96 | 8.67 | 1.85 |
| Found | 61.78 | 8.54 | 1.87 |

Spectral Data

NMR(CDCl$_3$):γ = 5.61(1H)bS; 5.53(1H)bS; 3.36(3H)S; 2.26(6H)S; 2.10(3H)S; 2.06(3H)S.

IR(CHCl$_3$): 5.75, 5.90 and 6.15μ

UV(CH$_3$OH): 225mμ; ε=5338 l/mole

In a similar fashion, the other 2',4" acyl esters of 8,8a-methylene-oleandomycin may be prepared from the corresponding 2',4" acyl esters of the natural epoxide compound having from two to three carbon atoms in the acyl groups.

EXAMPLE II 8,8a-Deoxy-8,8a-Methylene-2',4",11-Triacetyloleandomycin

A solution of 2',4",11-triacetyloleandomycin (500 g) in acetone (3.25 l) and water (1.75 l) was treated with a solution of chromous chloride [prepared by the method of Example I from chromium trichloride (1000 g), zinc dust (200 g) and mercuric chloride (20 g)] in a carbon dioxide atmosphere as described in Example I. The final ethyl acetate extracts (2500 ml) were concentrated to 800 ml and 3 volumes of heptane added and the crystallization allowed to proceed overnight to yield in two crops the title compound (426 g, m.p. 132°–134° C).

Elemental Analysis

|  | C | H | N |
|---|---|---|---|
| Calculated | 61.71 | 8.46 | 1.76 |
| Found | 61.59 | 8.42 | 1.72 |

Spectral Data

NMR(CDCl$_3$): δ = 5.86(1H)bS; 5.61(1H)bS; 3.33(3H)S; 2.26(6H)S; 2.06(6H)S; 2.01(3H)S.

IR(CHCl$_3$): 5.70, 5.90, 6.00 and 6.17μ.

UV(CH$_3$OH): 228mμ; ε = 5927 l/mole.

In a similar fashion, the other 2',4",11 acyl esters of 8,8a-methylene-oleandomycin, except those with a trifluoroacetoxy or a tri-(lower alkyl)silyloxy group at the 11-position, are prepared from the corresponding 2',4", 11 acyl esters of the natural epoxide compound having from two to three carbon atoms in the acyl group(s).

EXAMPLE III 8,8a-Deoxy-8,8a-Methylene-2'-Acetyloleandomycin

A solution of 2'-acetyloleandomycin (29.2 g) in acetone (200 ml) and water (100 ml) was mixed with a solution of chromous chloride [prepared from chromium trichloride (50 g), zinc dust (10 g) and mercuric chloride (1 g) by the method of Example I] in a carbon dioxide atmosphere as described in Example I. The final ethyl acetate extracts were concentrated to dryness under reduced pressure and the residue crystallized from ether/petroleum ether followed by recrystallization from ethyl acetate/petroleum ether to give the title compound (8.4g, m.p. 183.5°–185° C).

Elemental Analysis

|  | C | H | N |
|---|---|---|---|
| Calculated | 62.16 | 9.02 | 1.95 |
| Found | 61.97 | 8.91 | 2.01 |

Spectral Data

NMR(CDCl$_3$):δ = 5.63(1H)bS; 5.58(1H)bS; 3.43(3H)S; 2.36(6H)S; 2.08(3H)S.

IR(CHCl$_3$): 5.78, 5.90, 5.95 and 6.12μ

UV(CH$_3$OH): 224mμ; ε = 4468 l/mole.

In a similar fashion, the other 2'-acyl esters of 8,8a-methylene-oleandomycin are prepared from the corresponding 2'-acyl esters of the natural epoxide compound having from two to three carbon atoms in the acyl group.

EXAMPLE IV 8,8a-Deoxy-8,8a-Methylene-Oleandomycin

A solution of oleandomycin (5.0 g) in water (25 ml) adjusted to pH 3.5 with 1N HCl was mixed with a solution of chromous chloride [chromium trichloride (13 g), zinc dust (8 g) and mercuric chloride (700 mg), prepared by the method of Example I] in a carbon dioxide atmosphere. About half-way through the mixing acetone (20 ml) was added to the mixture and the additions continued. After 45 min. of stirring at room temperature, methylene chloride (100 ml) was added and the pH was adjusted to 8.5 with 8N sodium hydroxide. The organic phase was separated and the aqueous layer extracted with a second portion of methylene chloride (100 ml). The methylene chloride extracts were combined washed with water (100 ml), saturated sodium chloride (200 ml) and dried over anhydrous sodium sulfate and evaporated under reduced pressure. The residue was crystallized from chloroform by displacement with heptane to give the title compound (2.28 g, m.p. 120°–123° C).

Spectral Data

NMR(CDCl$_3$): = 5.63(1H)bS; 5.56(1H)bS; 3.41(3H)S; 2.30 (6H)S.

UV(CH$_3$OH): 223 mμ; ε =3900 l/mole.

EXAMPLE V

8,8a-Deoxy-8,8a-Methylene-2',4"-Diacetyl-11-Trifluoroacetyloleandomycin

To a flame dried 1 liter; three-necked round bottom flask equipped with a magnetic stirrer, dropping funnel and drying tube was added 8,8a-deoxy-8,8a-methylene-2',4"-diacetyloleandomycin (200 g) and trifluoroacetic anhydride (400 ml) at 5°–10° C. Pyridine (42.6 ml) was added over a 5 min. period and the reaction allowed to proceed overnight at room temperature. The reaction mixture was concentrated to an oil under reduced pressure and poured onto a mixture of ice and ethyl acetate. The pH was adjusted to pH 8.5 with aqueous sodium bicarbonate and the ethyl acetate phase separated washed with water, saturated sodium chloride and dried over anhydrous sodium sulfate. The solvent was evaporated under reduced pressure and the resulting foam crystallized from ethyl acetate/heptane to give the title compound (136 g, m.p. 169°–172° C).

Elemental Analysis

|            | C     | H    | N    |
|------------|-------|------|------|
| Calculated | 57.80 | 7.57 | 1.64 |
| Found      | 57.79 | 7.50 | 1.62 |

Spectral Data
NMR(CDCl$_3$): δ = 6.08(1H)S; 5.91(1H)S; 3.41(3H)S; 2.36 (6H)S; 2.16(6H)S.
IR(CHCl$_3$): 5.75, 5.85, 5.90 and 6.10μ

In a similar fashion, the other 2',4"-diacyloleandomycins of the present invention may be converted into the corresponding 2',4"-diacyl-11-trifluoroacetyloleandomycins having from two to three carbon atoms in the acyl group.

EXAMPLE VI

8,8a-Deoxy-8,8a-Methylene-2',4"-Diacetyl-11-Trifluoracetyloleandomycin

A solution of 8,8a-deoxy-8,8a-methylene-2',4"-diacetyloleandomycin (1.0 g) in 50 ml of benzene was treated with 0.20 ml of trifluoracetic anhydride and 0.11 ml of pyridine. The solution was allowed to stir at room temperature for 90 minutes and poured into water. Sodium bicarbonate solution was added to pH 8.5 and the organic layer separated, washed with water, saturated sodium chloride and dried over anhydrous sodium sulfate. Evaporation of the solvent under reduced pressure gave 8,8a-deoxy-8,8a-methylene-2',4"-diacetyl-11-trifluoroacetyloleandomycin identical by spectroscopic and thin layer chromatographic analysis with a specimen prepared by the method of Example V.

EXAMPLE VII

8,8a-Deoxy-8,8a-Methylene-2',11-Diacetyloleandomycin

To a stirred solution of 8,8a-deoxy-8,8a-methylene-2',4",11-triacetyloleandomycin in isopropyl alcohol (50 ml) at room temperature under nitrogen was added a solution of sodium isopropoxide in isoproyl alcohol (17.8 ml, 0.176M). After 3.5 hr another portion of the sodium isopropoxide solution (17.8 ml, 0.176M) was added and stirring contained for 1 hr at room temperature. The pale yellow solution was poured in water and extracted with ethyl acetate. The organic phase was separated washed successively with water, saturated sodium chloride, dried over sodium sulfate, filtered and evaporated. The resulting foam was crystallized from ethyl acetate: hexane to give the title compound (2.35 g, m.p. 117°–119°).

Spectral Data
NMR(CDCl$_3$): δ = 5.96(1H)bS; 5.73(1H)bS; 3.45(3H)S; 2.33(6H)S; and 2.10(3H)S.

In a similar fashion, the other 2',11-diacyloleandomycin of the present invention may be prepared from the corresponding 2',4",11-triacyloleandomycins having from two to three carbon atoms in the acyl group.

EXAMPLE VIII

8,8a-Deoxy-8,8a-Methylene-2',4"-Diacetyl-11-Trimethylsilyloleandomycin

In a flame dried 100 ml, three-necked round bottom flask equipped with magnetic stirrer and drying tube, a suspension of 8,8a-deoxy-8,8a-methylene-2',4"-diacetyloleandomycin (20 g), and imidazole (4.5 g) in dry dimethylformamide (32 ml) was treated with trimethylsilyl chloride (6.72 ml) and stirred at room temperature for 90 min. The pale yellow solution was poured into water (300 ml) and ethyl acetate (300 ml) and adjusted to pH 10.5 with 4N sodium hydroxide. The aqueous phase was separated and ethyl acetate washed with water (300 ml), saturated sodium chloride (300 ml), dried over anhydrous sodium sulfate and evaporated under reduced pressure to a white foam (22 g), homogeneous by thin layer chromatography (silica gel plates eluted with: ethylacetate: acetone 3:1, R$_f$ 0.6; carbon tetrachloride:diethylamine 9:1, R$_f$ 0.7).

Spectral Data
NMR(CDCl$_3$):δ = 6.00(1H)bS; 5.73(1H)bS; 3.36(3H)S; 2.33(6H)S; 2.13(6H)S; 0.16(9H)S.

In a similar fashion, the tri(lower alkyl) silyl homologs of the title compound may be produced. Also, this procedure can be used to prepare the 11-tri(lower alkyl) silyl derivatives of the other 2',4"-acyloleandomycins of the present invention having from two to three carbon atoms in the acyl group.

EXAMPLE IX

8,8a-Deoxy-8,8a-Cyclopropyl-2',4",11-Triacetyloleandomycin

In a flame dried 1 liter three-necked round bottom flask equipped with a dropping funnel, magentic stirrer and a positivepressure nitrogen inlet was combined 18.2 g (83 mmoles) of trimethylsulfoxonium iodide and 3.98 g (83 mmoles) of a 50% oil dispersion of sodium hydride. The solids were mixed well and 80 ml of dimethylsulfoxide (DMSO) was added via a dropping funnel over 5–7 minutes with cooling in an ice/water bath. The reaction mixture was allowed to stir at room temperature until the evolution of hydrogen stopped, about one hour. A solution of 50 g (63 mmoles) of 8,8a-deoxy-8,8a-methylene-2',4",11-triacetyloleandomycin in 60 ml of tetrahydrofuran (THF) and 30 ml of DMSO was added dropwise over 5–7 minutes and the reaction allowed to proceed at room temperature for 1 hour. The solution was poured into a mixture of water/ethyl acetate and the aqueous phase adjusted to pH 9. The organic phase was separated washed with water, saturated solution of sodium chloride, dried over sodium sulfate, filtered and evaporated to dryness under reduced pressure. The residue was crystallized from ethyl acetate/heptane to yield 25.8 g of 8,8a-deoxy-8,8a-cyclopropyl-2',4",11- triacetyloleandomycin, mp 119°-129° C; this material contains a small amount (~ 5-10%) of the C$_4''$-deacetyl compound 8,8a-deoxy-8,8a-cyclopropyl-2',11-diacetyloleandomycin, but is sufficiently pure for use in subsequent chemical transformations. Chromatography of an aliquot of the material melting 119°-129° C on silica gel using the solvent system ethyl acetate/isopropyl alcohol (9:1), followed by crystallization from ethyl acetate/heptane affords a homogeneous sample of 8,8a-deoxy-8,8a-cyclopropyl-2,4'',11-triacetyloleandomycin, m.p. 142.5°-144.5° C, showing the following characteristic peaks in the nmr:

(CDCl$_3$) γ = 3.35 (3H)S; 2.26 (6H)S; 2.10 (6H)S; 2.03 (3H)S; 0.60 (4H)M.

EXAMPLE X 8,8a-Deoxy-8,8a-Cyclopropyl-11-Acetyloleandomycin

A solution of 12.0 g (14.8 mmoles) of 8,8a-deoxy-8,8a-cyclopropyl-2',4'',11-triacetyloleandomycin in 300 ml of methanol was treated with 719 mg (17.1 mmoles) of lithium hydroxide monohydrate and the clear colorless solution was allowed to stir at room temperature under nitrogen overnight. The solution was evaporated to dryness under reduced pressure and the resulting white foam was taken up in a mixture of water and ethyl acetate and adjusted to pH 9. The organic phase was separated washed with water, saturated sodium chloride, dried over anhydrous sodium sulfate, filtered and evaporated to yield a white foam which was crystallized from acetone/heptane giving 8.8 g of 8,8a-deoxy-8,8a-cyclopropyl-11-acetyloleandomycin, m.p. 121.5°-123.5°, and showing the following characteristic peaks in the nmr:

(CDCl$_3$) γ = 4.20 (1H) D; 3.40 (3H) S; 2.28 (6H) S; 2.03 (3H) S; 0.55 (4H) M;

EXAMPLE XI 8,8a-Deoxy-8,8a-Cyclopropyl-11-Acetyloleandomycin

A solution of 8,8a-deoxy-8,8a-cyclopropyl-2,11-diacetyloleandomycin (1.3 gm, 1.16 mmoles) in methanol was stirred overnight, evaporated to dryness under reduced pressure and the residue crystallized from acetone/heptane to give 800 mg of 8,8a-deoxy-8,8a-cyclopropyl-11-acetyloleandomycin, m.p. 123°-125°, identical by thin layer chromatography and nmr with material prepared by the lithium hydroxide procedure.

EXAMPLE XII 8,8a-Deoxy-8,8a-Cyclopropyl-4'',11-Diacetyloleandomycin

A solution of 8,8a-deoxy-8,8a-cyclopropyl-2',4'''-11-triacetyloleandomycin (1.5 g, 1.85 mmoles) in methanol was stirred overnight, evaporated to dryness under reduced pressure and the residue crystallized from ether/heptane to give 1.3 g of 8,8a-deoxy,8,8a-cyclopropyl-4'',11-diacetyloleandomycin, m.p. 159°-161.5° C, which shows the following characteristic peaks in the nmr:

(CDCl$_3$) γ = 3.35 (3H) S; 2.30 (6H) S; 2.09 (3H) S; 2.04 (3H) S; 0.58 (4H) M.

EXAMPLE XIII 8,8a-Deoxy-8,8a-Cyclopropyl-2',11-Diacetyloleandomycin

In a flame dried 200 ml three-necked flask equipped with a dropping funnel, magnetic stirrer and a positive-pressure nitrogen inlet was combined 16.4 g (74.8 mmoles) of trimethylsulfoxonium iodide and 3.4 g (74.8 mmoles) of a 50% oil dispersion of sodium hydride. The solids were mixed well and 43.2 ml of DMSO was added via the dropping funnel. After one hour, when the evolution of hydrogen had stopped, the suspension was cooled to 5°-10° C and a solution of 22.6 g (30 mmoles) of 8,8a-deoxy-8,8a-methylene-2',11-diacetyloleandomycin in 32 ml of THF and 16 ml of DMSO was added over a 10 minute period. The suspension was stirred at room temperature for 90 minutes and poured in 300 ml of water and extracted with two 300 ml portions of ethyl acetate. The organic extracts were washed with water, saturated solution of sodium chloride, dried over anhydrous sodium sulfate, filtered, and evaporated to dryness under reduced pressure. The residue was crystallized from ether to give 8.9 g of 8,8a-deoxy-8,8a-cyclopropyl-2',11-diacetyloleandomycin identical by thin layer chromatography and nmr with material prepared by the sodium isopropoxide procedure on 8,8a-deoxy-8,8a-cyclopropyl-2',4'',11-triacetyloleandomycin.

EXAMPLE XIV 8,8a-Deoxy-8,8a-Cyclopropyl-2,11-Diacetyloleandomycin

In a 12-liter three-necked round bottom flask, flame dried and equipped with a mechanical stirrer and positive pressure nitrogen inlet was dissolved 306 g (0.376 mmoles) of 8,8a-deoxy-8,8a-cyclopropyl-2',4'',11-triacetyloleandomycin in 3 liters in isopropyl alcohol. To this solution was added over a 10 minute period 1230 ml (0.376 mmoles) of a 0.3 M solution of sodium isopropoxide in isopropyl alcohol. After 30 minutes, 3 liters of water was added the solution adjusted to pH 7.0 and concentrated under reduced pressure to approximately one-half volume, poured into ethyl acetate and readjusted to pH 9.5. The organic layer was separated, washed with water, saturated solution of sodium chloride, dried over sodium sulfate, filtered and evaporated under reduced pressure. The resulting foam was dissolved in 2 liters of benzene and treated with 7.0 ml of acetic anhydride. After one hour at room temperature the solution was treated with additional 7.0 ml of acetic anhydride and after stirring 45 minutes more was poured into 2 liters of water, the pH adjusted to 7.0 with solid sodium tricarbonate and to 9.5 with 4N sodium hydroxide. The organic layer was separated, washed with water, saturated solution of sodium chloride, dried over anhydrous sodium sulfate, filtered and evaporated to dryness under reduced pressure. The residue was crystallized from ether to give 159 g of 8,8a-deoxy-8,8a-cyclopropyl-2',11-diacetyloleandomycin, m.p. 159°-162° C, and showing the following characteristic peaks in the nmr:

(CDCl$_2$) γ: = 3.43 (3H) S; 2.28 (6H) S; 2.10 (3H) S; 2.03 (3H) S; 0.56 (4H) M.

EXAMPLE XV 8,8a-Deoxy-8,8a-Cyclopropyl-2',4''-Diacetyloleandomycin

A solution of 8,8a-deoxy-8,8a-cyclopropyl-2',4''-diacetyl-11-trimethylsilyloleandomycin (4.6 g, 5.46 mmoles) in 100 ml of 30% aqueous tetrahydrofuran adjusted to pH 2.0 with acid was stirred for 1 hour at room temperature, the pH adjusted to 6.9 and the tetrahydrofuran evaporated under reduced pressure. The resulting material was added to a mixture of ethyl acetate and water and the pH adjusted to 9. The ethyl acetate phase was separated, washed with water, saturated sodium chloride, dried over sodium sulfate, filtered and evaporated under reduced pressure to a white foam (4.0 g). Chromatography of 3.4 g of this material on 120 g of silica gel eluting with the solvent system benzene/acetone (4:1) gave 2.5 g of 8,8a-deoxy-8,8a-cyclopropyl-2',4"-diacetyloleandomycin as a white foam, homogeneous in the TLC systems ethyl acetate/acetone (3:1) and carbontetrachloride/diethylamine (9:1) and carbontetrachloride/diethylamine (9:1) (Brinkman silica gel plates) and exhibiting the following peaks in the nmr:

(CDCl$_3$) $\gamma$ = 5.45 (1H) M; 3.35 (3H) S; 2.25 (6H) S; 2.08 (6H) S; 0.65 (4H) M.

EXAMPLE XVI 8,8a-Deoxy-8,8a-Cyclopropyloleandomycin

To a solution of 19 g (22.5 mmoles) of 8,8a-deoxy-8,8a-cyclopropyl-2',4"-diacetyl-11-trimethylsilyloleandomycin in 1 liter of methanol in a flame dried 2 liter single necked round bottom flask equipped with magnetic stirrer and nitrogen inlet was added 3.12 g (22.5 mmoles) of potassium carbonate and the solution allowed to stir at room temperature overnight. This solution was adjusted to pH 2.0 with 1N hydrochloride (~ 50 ml) and the solution stirrer at room temperature for 40 minutes. The solution was adjusted to pH 6.9 and the methanol evaporated under reduced pressure. The residue was distributed between ethyl acetate/water, pH adjusted to 9.0 and the organic later separated, washed with water, saturated sodium chloride, dried over sodium sulfate, filtered and evaporated to a white foam (12 g). This material was chromatography on 300 g of silica gel eluted with chloroform/methanol (19:1) and the desired fractions combined and evaporated to give 5.6 g of 8,8a-deoxy-8,8a-cyclopropyloleandomycin as a white foam. This material is homogeneous in the TLC (Brinkmann silica gel plates) systems ethyl acetate/methanol (1:1), carbon tetrachloride/diethylamine (9:1) and chloroform/methanol (4:1), and exhibits the following characteristics peaks in the nmr:

(CDCl$_3$) $\gamma$ = 5.45 (1H9 ; 4.93 (1H) M; 4.13 (1H) D; 3.40 (3H) S; 2.26 (6H) S; 0.63 (4H) M.

EXAMPLE XVII 8,8a-Deoxy-8,8a-Cyclopropyl-2'-Acetyloleandomycin

To a stirred solution of 8,8a-deoxy-8,8a-cyclopropyloleandomycin (184 mg, 0.26 mmoles) in 18 ml of benzene was added 27.8 μl (0.295 mmoles) of acetic anhydride. The solution was allowed to stir at room temperature under nitrogen for two hours, poured into a mixture of water and ethyl acetate and adjusted to pH 9. The organic layer was separated washed with water, saturated sodium chloride, dried over sodium sulfate, filtered and evaporated under reduced pressure to 173 mg of 8,8a-deoxy-8,8a-cyclopropyl-2'-acetyloleandomycin showing the following characteristic peaks in nmr:

(CDCl$_3$) $\gamma$ = 5.45 (1H) M; 3.38 (3H) S; 2.25 (6H) S; 2.05 (3H) S; 0.65 (4H) M.

EXAMLE XVIII 8,8a-Deoxy-8,8a-Cyproyl-2',4"-Diacetyl-11-Trimethylsilyloleandomycin.

In a flame dried, 75 ml, three-necked round bottom flask equipped with a magnetic stirrer, serum stopper and positive nitrogen hook-up was mixed 1.20 g (5.46 mmoles) trimethylsulfoxonium iodide and 262 mg (5.46 mmoles) of 50% oil dispersion sodium hydride. The mixture was cooled in an ice/water bath and 13 ml of dimethylsulfoxide was added via syringe over 1 minute period. Vigorous hydrogen evolution was noted. The cooling bath was removed and stirring continued for 45 minutes to yield the ylid as a pale tan solution. This solution was cooled in an ice/water bath and a solution of 3.62 g (4.37 mmoles) of 8,8a-deoxy-8,8a-methylene-2',4"-diacetyl-11-trimethylsilyloleandomycin in 22 ml of tetrahydrofuran (seive dried) was added via syringe, washing in with an additional 8 ml of dry tetrahydrofuran. The addition was made over a 1 minute period after the cooling bath was removed and the white suspension allowed to stir at room temperature for 1 hour and 40 minutes. The mixture was poured into 100 ml of water and 100 ml of ethyl acetate and the aqueous phase was separated. The organic phase was washed with one volume of water, one volume of saturated sodium chloride dried over anhydrous sodium sulfate, filtered and evaporated under reduced pressure to yield 3.3 g of white foam. This material is homogeneous in the chromatography systems ethyl acetate/acetone (3:1) and carbon tetrachloride/diethylamine (9:1) on Brinkman silica gel plates. It exhibits the following characteristic peaks in nmr:

(CDCl$_3$ $\gamma$ = 3.40 (3H) S; 2.33 (6H) S; 2.15 (3H) S; 2.13 (3H) S; 0.58 (4H) M; 0.15 (9H) S.

EXAMPLE XIX 8,8a-Deoxy-8,8a-Cyclopropyl-4"-Acetyloleandomycin

A solution of 1.0 g (1.3 mmoles) of 8,8a-deoxy-8,8a-cyclopropyl-2',4"-diacetyloleandomycin in 100 m of methanol was stirred overnight at room temperature. The solvent was evaporated under reduced pressure to give 1.0 g of 8,8a-deoxy-8,8a-cyclopropyl-4"-acetyloleandomycin as a white foam homogeneous in the thin layer chromatography systems ethylacetate/acetone (3:1) and carbon tetrachloride/diethylamine (9:1) (Brinkman silica gel plates) and showing the following peaks in the nmr:

(CDCl$_3$) $\gamma$ = 5.43 (1H) M; 3.33 (3H) S; 2.26 (6H) S; 2.06 (3H) S; 0.63 (4H) M.

What is claimed is:

1. A compound of the formula

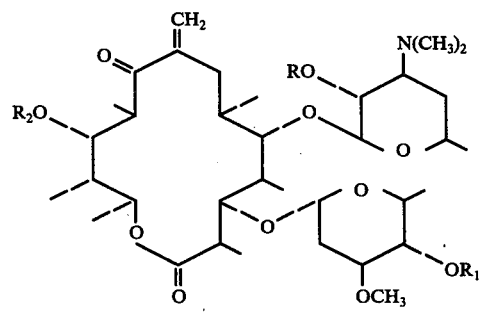

and the pharmaceutically acceptable mineral or organic addition salts thereof wherein R is selected from the group consisting of hydrogen, and alkanoyl having from two to three carbon atoms; $R_1$ is selected from the group consisting of hydrogen alkanoyl having from two to three carbon atoms and tri-(lower-alkyl) silyl; and $R_2$ is selected from the group consisting of hydrogen, alkanoyl having from two to three carbon atoms, trifluoroacetyl and tri(lower alkyl)silyl.

2. The compound of claim 1 wherein R and $R_1$ are acetyl and $R_2$ is acetyl, trifluoroacetyl or trimethylsilyl.

3. A compound of the formula

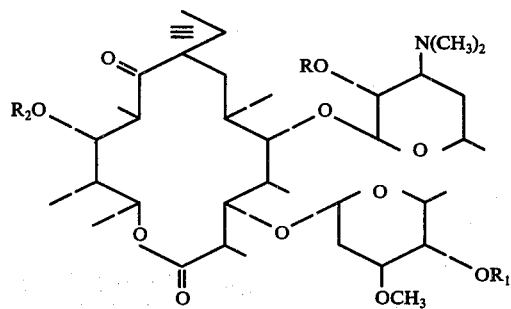

and the non-toxic acid addition salts thereof wherein R is selected from the group consisting of hydrogen and alkanoyl having from two to three carbon atoms; and $R_1$ and $R_2$ are selected from the group consisting of hydrogen, alkanoyl having from two to three carbon atoms and tri-(lower alkyl)silyl.

4. A compound of claim 3 wherein R and $R_1$ are hydrogen and $R_2$ is hydrogen or acetyl.

5. A process for preparing a compound of the formula

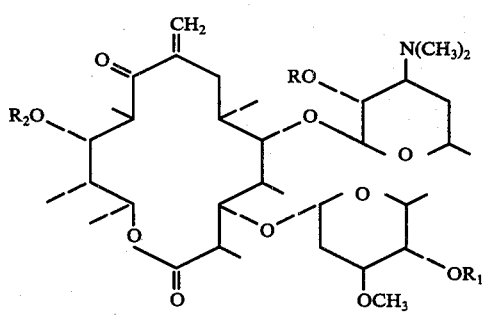

wherein R, $R_1$ and $R_2$ are selected from the group consisting of hydrogen and alkanoyl having from two to three carbon atoms which comprises contacting a compound of the formula

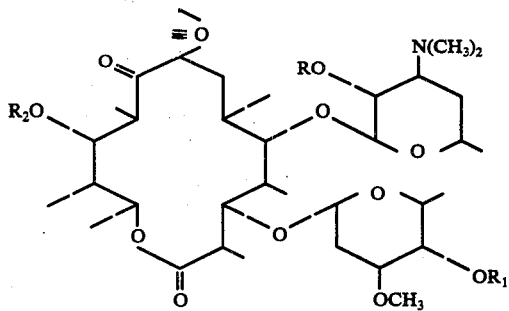

wherein R, $R_1$ and $R_2$ are as defined above in a water miscible, reaction-inert solvent with lower valence state transition metal ions selected from the group consisting of $Cr^{+2}$, $Ti^{+3}$ and $V^{+2}$ until the reaction is substantially complete.

6. The process of claim 5 wherein said water miscible, reaction-inert solvent is selected from the group consisting of acetone, a lower alkanol, tetrahydrofuran and mixtures thereof.

7. A process for preparing a compound of the formula

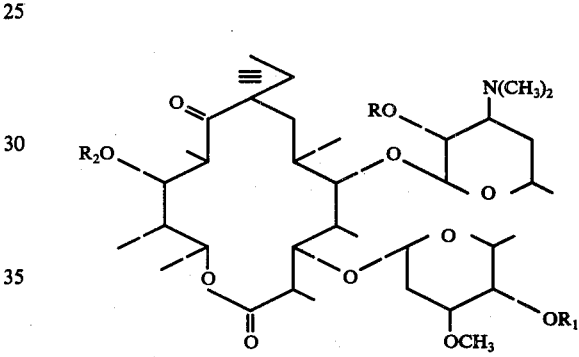

wherein R is alkanoyl having from two to three carbon atoms; $R_1$ is selected from the group consisting of hydrogen, alkanoyl having from two to three carbon atoms and tri-(lower alkyl) silyl; and $R_2$ is selected from the group consisting of alkanoyl having from two to three carbon atoms and tri-(lower alkyl)silyl which comprises, while stirring, reacting a compound of the formula

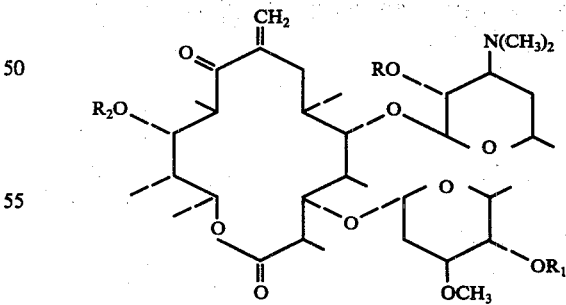

wherein R, $R_1$ and $R_2$ are as defined above in a reaction-inert solvent with cooling in ice/water with at least a substantially equivalent amount of dimethylsulfoxonium methylide and then allowing the mixture to come to room temperature.

8. The process of claim 7 wherein the reaction-inert solvent is selected from the group consisting of dimethylsulfoxide, tetrahydrofuran and mixtures thereof.

* * * * *